United States Patent [19]

Eckenhoff

[11] 4,299,222
[45] Nov. 10, 1981

[54] SELF-CONTAINED SUCTION PUMP

[75] Inventor: James B. Eckenhoff, Los Altos, Calif.

[73] Assignee: ALZA Corporation, Palo Alto, Calif.

[21] Appl. No.: 110,376

[22] Filed: Jan. 8, 1980

[51] Int. Cl.³ .............................................. A61M 1/00
[52] U.S. Cl. ..................................... 128/278; 128/760
[58] Field of Search ............................ 141/110, 65, 8; 210/644, 321.1; 433 M; 417/572; 137/122, 147; 128/760, 767, 768, 769, 230, 273, 276–278, 296, 297

[56] References Cited

U.S. PATENT DOCUMENTS

| | | | |
|---|---|---|---|
| 3,032,037 | 5/1962 | Huber | 128/276 |
| 3,485,751 | 12/1969 | Herrmann et al. | 128/767 X |
| 3,760,805 | 9/1973 | Higuchi | 128/260 |
| 3,865,108 | 2/1975 | Hartop | 128/260 |
| 3,880,164 | 4/1975 | Stepno | 128/276 |
| 3,987,790 | 10/1976 | Eckenhoff et al. | 128/260 |
| 4,034,756 | 7/1977 | Higuchi et al. | 128/260 |

Primary Examiner—Robert W. Michell
Assistant Examiner—J. E. Hanley
Attorney, Agent, or Firm—Paul L. Sabatine; Edward L. Mandell

[57] ABSTRACT

A small suction pump that may be implanted in test animals to draw biological fluid samples is disclosed. The pump, before it is activated, consists of an outer, impermeable expansible housing, an inner, expanded elastomeric fluid collection container housed within the housing, a port extending from the container lumen through the housing, a rigid semipermeable partition between the housing and inner container, and a water-imbibing composition interposed between the housing and the partition. The pump is activated by charging water between the partition and container. Such charging of water forces the container to collapse. In operation water is drawn through the partition by the water imbibing composition thereby permitting the container to expand and suck fluid via the port.

3 Claims, 4 Drawing Figures

SELF-CONTAINED SUCTION PUMP

TECHNICAL FIELD

The invention relates to a self-contained suction pump for drawing small samples of fluid.

DISCLOSURE OF PRIOR ART

Osmotically driven, positive action pumps that displace liquids are described in U.S. Pat. Nos. 3,987,790 and 4,034,756. A commercial embodiment of the pumps described in those patents is marketed as the ALZET® minipump. The ALZET® minipump consists of an outer rigid semipermeable housing, an inner collapsible bag contained within the housing and an osmotically effective solute interposed between the housing and the inner bag. Liquid to be displaced is charged into the inner bag and the minipump is placed in a water-containing environment. Water from the environment diffuses through the housing and dissolves the solute. The osmotic pressure imbalance between the resulting solution and the water in the environment causes water to be imbibed through the housing into the space between it and the bag. This influx of water exerts pressure on the bag causing it to collapse and the liquid charge to be squeezed therefrom through an outlet port.

U.S. Pat. No. 3,865,108 describes a device that squeezes fluid from a collapsible bag in response to the absorption of water by a water swellable material.

U.S. Pat. No. 3,880,164 describes an osmotically driven device for evacuating fluids from body cavities or wounds. The device comprises a fluid collection container that is divided into two compartments by a flexible water-impermeable partition and a semipermeable conduit that connects to one of the container compartments and extends to the fluid collection site. The conduit and container compartment to which it is connected contain a solution that has a higher osmotic pressure than the body fluid to be collected (about 7.5 atm). The other compartment is empty. Body fluids are drawn into the conduit and hence into the solution filled compartment by osmosis. The influx of fluid causes the partition to displace into the empty compartment, thereby accommodating the incoming water.

DISCLOSURE OF THE INVENTION

The invention is a self-contained suction pump for drawing a fluid, such as a small sample of biological fluid from an animal body. The components of the pump are: an outer impermeable expansible housing; an inner elastomeric fluid collection container in at least a partially collapsed state sealingly housed within the housing; a port extending from the container lumen through the housing; a rigid semipermeable partition between the housing interior and the container exterior; a water imbibing composition interposed between the housing and partition; and an aqueous fluid in the space between the at least partially collapsed container and the partition. Before the pump is activated, the container is expanded (not partially collapsed) and the aqueous fluid is absent. The pump is activated by charging the aqueous fluid between the partition and container. The charging of water to the pump forces the container to collapse.

DESCRIPTION OF THE PREFERRED EMBODIMENT

Figure 1:
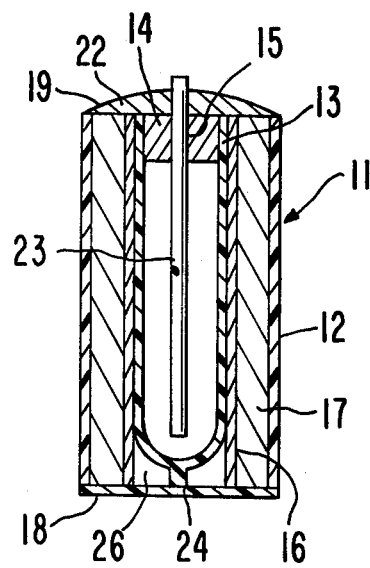
FIG. 1 is a vertical sectional view of the preferred embodiment of the pump before it is charged with water to activate it.

The preferred embodiment of the pump is generally designated 11 in the drawings. Pump 11 is generally cylindrical in shape. FIG. 1 shows the basic elements of the pump before it is activated by the addition of water. Those elements are: an outer, impermeable, expansible housing 12; an inner elastomeric, impermeable liquid collection container 13; a plug 14 closing one end of the container and having a central bore 15 through it; a rigid semipermeable partition 16 surrounding and located outwardly of container 13; a layer 17 of a water imbibing composition interposed between housing 12 and partition 16, a bottom wall 18 that is water impermeable and is penetrable by a syringe and self-sealing after withdrawal of the syringe; and a flow moderator 19 that comprises a head 22 that seals the end of the pump opposite bottom wall 18 and a tube 23 that extends through head 22 and bore 15 and down into container 13. The bottom of container 13 is connected to bottom wall 18 by a nub 24 that is adhered, fused, or otherwise affixed to wall 18. Such connection keeps container 13 extended axially within housing 12.

Housing 12 may be made from a variety of known, available water impermeable elastomers. Examples of elastomers from which the housing may be made are polyisoprene, natural rubber, nitrile rubber, butyl rubber, and styrene-butadiene copolymers. The material from which the housing is made and the thickness of the housing are such that the housing readily expands in response to the hydrostatic pressure generated by the imbibition of water by layer 17. Preferably the housing will be made of a styrene-butadiene copolymer and be from 0.4 to 0.8 mm thick.

Container 13 may be made from the materials that may be used to make housing 12. The container must be capable of collapsing as water is injected into the space between it and partition 16 and expanding as water is evacuated from that space. Bottom wall 18 may likewise be made from these materials.

Partition 16 may also be made from known, available polymers that are semipermeable and that can be formed into a rigid film or membrane that is chemically and physically stable in the presence of water and, when the water imbibing composition is a solute, in the presence of concentrated solution of the solute. Polymers that are used to make osmosis and reverse osmosis membranes are one group of materials that may normally be employed to make the partition. Such materials include cellulose acetate, cellulose acetate butyrate and other cellulose esters. Preferably the polymer that is used to make the partition will have a water vapor transmission rate in the range of $1 \times 10^{-6}$ to $15 \times 10^{-6}$ cc (@ STP)·cm/cm$^2$·sec·cm Hg.

The layer of water-imbibing composition must be capable of taking up a significant portion, and preferably substantially all, of the water that is injected into the space between container 13 and partition 16 to activate the pump. Osmotically effective solutes that may be used should have an osmotic pressure in solution that substantially exceeds the osmotic pressure of water. Such solutes include inorganic salts, organic salts and sugars. Examples of same are the inorganic salts of alkali metals and alkaline earth metals such as sodium chloride, potassium chloride, lithium chloride, magnesium sulfate, sodium carbonate, sodium sulfite, and potassium acid phosphate, the alkali metal and alkaline earth metal salts of fatty acids such as calcium lactate, magnesium succinate, and sodium tartrate, and the simple sugars such as lactose, fructose, dextrose, sucrose, and mannitol. Mixtures of such solutes may be used if desired.

The water swellable materials that may be used to make layer 17 are capable of absorbing water and increasing in volume significantly. Preferably they are capable of absorbing at least about 50% of their own weight in water. Examples of such materials are disclosed in U.S. Pat. No. 3,865,108, col. 2, line 35–49. That disclosure is incorporated herein by reference.

Plug 14 may be made from the same material from which the housing is made, provided the dimensions of the plug are such as to render it substantially inexpandible. Otherwise the plug may be made from polymers that are substantially rigid. Whatever material is used, it must be capable of being adhered, fused or otherwise affixed within the end of container 13 to effectively seal the end thereof.

Flow moderator 19 may be made from various metallic or polymeric materials that are compatible with the site at which the pump is to be used. For instance, if the pump is to be placed within the body of an animal, the flow moderator should be compatible (i.e. nontoxic and nonirritating) to the tissues and fluids of the animal. Flow moderators are described in the above-mentioned U.S. Pat. No. 4,034,756 relating to the ALZET ® minipump. The disclosure of said patent, as it relates to comparable elements of the invention pump, is incorporated herein by reference.

Figure 2:
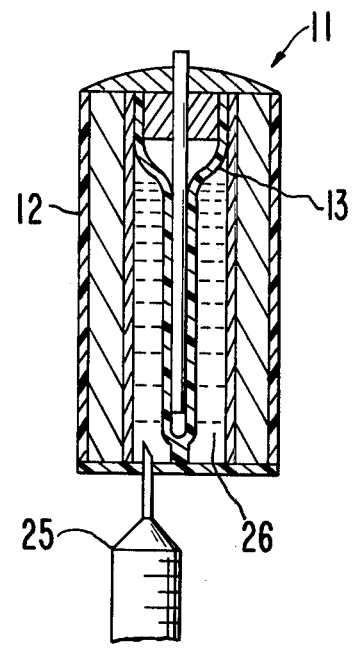
FIG. 2 is a vertical sectional view of the pump of FIG. 1 being charged with water to prepare it for operation.
Figure 3:
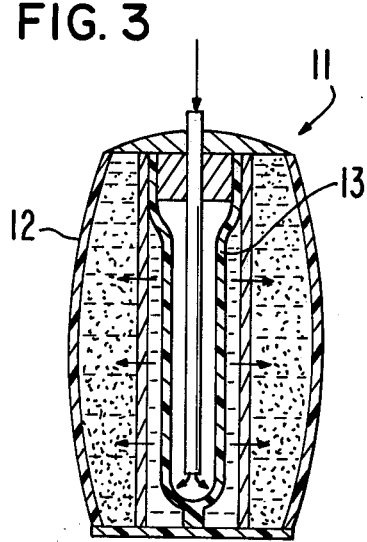
FIG. 3 is a schematic, vertical sectional view of the pump of FIG. 1 during operation.
Figure 4:
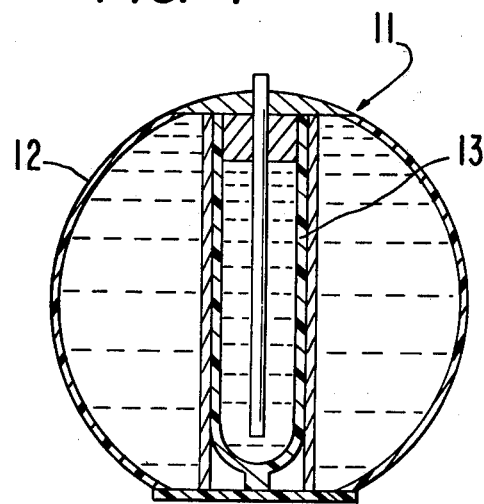
FIG. 4 is a vertical sectional view of the pump of FIG. 1 at the end of its operation.

Pump 11 is operated as follows. If the pump is to be located remote from the source of liquid to be drawn, one end of a conduit (not shown) is attached to the exterior end of tube 23 and the other end is placed in contact with the liquid to be drawn. If the pump is to be placed in the source it is not necessary to attach a conduit to tube 23. As shown in FIG. 2, the pump is activated by injecting the needle of a water-filled syringe 25 through wall 18 into space 26 between container 13 and partition 16 and filling that space with water from the syringe. After space 26 is filled with water the syringe is removed and wall 18, being made from an elastomer, seals itself. The injection of water into space 26 forces container 13 to collapse inwardly. Water from space 26 then diffuses through semipermeable partition 16 into the space occupied by layer 17. The movement of water through partition 16 is represented by arrows in FIG. 3. If layer 17 is composed of an osmotic solute, this water dissolves the osmotic solute and the osmotic pressure imbalance between the resulting solution and the water in the latter space creates hydrostatic pressure therein, thereby forcing housing 12 to expand outwardly. Housing 12 is depicted in a partly expanded state in FIG. 3. The evacuation of water from space 26 permits elastomeric container 13 to expand. The expansion of container 13 creates suction within tube 23 which draws liquid from the source into tube 23 and thence into container 13. The drawing action is represented in FIG. 3 by arrows entering and exiting tube 23. Liquid continues to be sucked into the pump until substantially all the water has been imbibed from space 26 and container 13 reaches its relaxed, expanded state, shown in FIG. 4. During the operation of the pump housing 12 expands outwardly to accomodate the continuous influx of water into the space occupied by layer 17. Once pump 11 reaches the condition shown in FIG. 4 it automatically shuts off. Flow moderator 19 prevents any significant diffusion of liquid from container 13 once the pump has shut off. Liquid may be removed from container 13 for analysis by drawing it therefrom with a syringe or other like instrument. Thus, pump 11 may be used to draw a known quantity of liquid equal to the filled volume of container 13 minus its collapsed volume continuously over a defined time period that depends on the permeability of partition 16 to water. As such, pump 11 is particularly useful for obtaining samples of biological fluids from humans or other animals.

Modifications of the above described pump that are obvious to those of skill in the fluid sampling and/or physiochemical arts are intended to be within the scope of the following claims.

I claim:

1. A self-contained suction pump for drawing a fluid comprising:
    (a) an outer impermeable expansible housing;
    (b) an inner elastomeric fluid collection container in at least a partially collapsed state sealingly housed within the housing;
    (c) a port extending from the container through the housing;
    (d) a rigid semipermeable partition between the housing interior and the container exterior, said partition substantially surrounding said container and being spaced therefrom;
    (e) a water imbibing composition interposed between the housing and partition; and
    (f) means for infecting an aqueous fluid in the space between the at least partially collapsed container and the partition.

2. The pump of claim 1 wherein the water-imbibing composition is an osmotically effective solute which, in solution, exhibits a greater osmotic pressure than the aqueous liquid within the container.

3. The pump of claim 1 wherein the water-imbibing composition is a water-swellable material.

* * * * *